US008001830B2

(12) United States Patent
Dazzi et al.

(10) Patent No.: US 8,001,830 B2
(45) Date of Patent: Aug. 23, 2011

(54) HIGH FREQUENCY DEFLECTION MEASUREMENT OF IR ABSORPTION

(75) Inventors: Alexandre Dazzi, Les Ulis (FR); Rui Prazeres, Bullion (FR); Kevin Kjoller, Santa Barbara, CA (US); Michael Reading, Norwich (GB)

(73) Assignee: Anasys Instruments, Inc., Santa Barbara, CA (US)

( * ) Notice: Subject to any disclaimer, the term of this patent is extended or adjusted under 35 U.S.C. 154(b) by 775 days.

(21) Appl. No.: 11/803,421

(22) Filed: May 15, 2007

(65) Prior Publication Data

US 2008/0283755 A1 Nov. 20, 2008

(51) Int. Cl.
*G01B 5/28* (2006.01)
*G01N 21/84* (2006.01)
*G01Q 80/00* (2010.01)

(52) U.S. Cl. .................. 73/105; 850/21; 850/33; 850/62

(58) Field of Classification Search .................... 73/105; 850/21, 22, 33, 62, 63
See application file for complete search history.

(56) References Cited

U.S. PATENT DOCUMENTS

| 5,193,385 | A * | 3/1993 | Nishioka et al. .............. 73/105 |
| 6,369,379 | B1 * | 4/2002 | Kley .............................. 250/234 |
| 7,497,613 | B2 * | 3/2009 | King et al. ..................... 374/141 |
| 2006/0222047 | A1 | 10/2006 | Reading | |
| 2010/0017922 | A1 * | 1/2010 | Shin et al. .................... 850/21 |

OTHER PUBLICATIONS

Unger, M.A. et al., "Etched Chalacogenide Fibers for Near-field Infrared Scanning Microscopy", Review of Scientific Instruments, vol. 69, No. 8, Aug. 1998, pp. 2988-2993.*
Samson, J. et al., "Setup of a Scanning Near Field Infrared Microscope (SNIM): Imaging of Sub-Surface Nano-Structures in Gallium-Doped Silicon", Physical Chemistry Chemistry Physics, vol. 8, 2006, pp. 753-758.*
Liu, Y. e tal., "A Stdy of Alkyl Chain Conformational Changes in Self-Assembled n-Octadecyltrichlorosilane Monolayers on Fused Silica Surfaces", Langmuir, vol. 17, 2001, pp. 4329-4335.*
A. Dazzi, R. Prazeres, F. Glotin, and J.M. Ortega, Local infrared microspectroscopy, with subwavelength spatial resolution with an atomic force microscope tip used as aphotothermal sensor, Optics Letters, vol. 30, No. 18, Sep. 15, 2005.
A. Dazzi, R. Prazeres, F. Glotin, and J.M. Ortega, Subwavelength infrared spectromicroscopy using an AFM as a local absorption Sensor, Infrared Physics and Technology, vol. 49, issues 1-2, Sep. 2006, pp. 113-121.
A. Dazzi, S. Goumri-Said, L. Salomon, Theoretical study of an absorbing sample in infrared near field spectromicroscopy, Optics Communications Feb. 2004.
A. Dazzi, R. Prazeres, F. Glotin, and J.M. Ortega, Analysis of nano-chemical mapping performed by an AFM-based ("AFMIR") acousto-optic technique, Ultramicroscopy, published on line Feb. 23, 2007.

* cited by examiner

*Primary Examiner* — Daniel S Larkin
(74) *Attorney, Agent, or Firm* — Mark Rodgers (57) ABSTRACT

An AFM based technique has been demonstrated for performing highly localized IR spectroscopy on a sample surface. Such a technique implemented in a commercially viable analytical instrument would be extremely useful. Various aspects of the experimental set-up have to be changed to create a commercial version. The invention addresses many of these issues thereby producing a version of the analytical technique that cab be made generally available to the scientific community.

8 Claims, 8 Drawing Sheets

HIGH FREQUENCY DEFLECTION MEASUREMENT OF IR ABSORPTION

RELATED APPLICATIONS

Not Applicable

FEDERALLY SPONSORED RESEARCH

Not Applicable

SEQUENCE LISTING

Not Applicable

BACKGROUND OF THE INVENTION

This invention is related to highly localized Infrared (IR) spectra on a sample surface utilizing an Atomic Force Microscope (AFM) and a variable wavelength pulsed IR source.

IR spectroscopy is a useful tool in many analytical fields such as polymer science and biology. It would be particularly useful to perform IR spectroscopy on a highly localized scale, on the order of biological organelles or smaller, at various points on a sample surface. Such a capability would provide information about the composition of surfaces, such as location of different materials or molecular structures. Recently, one of the inventors has developed a technique based on use of an AFM in a unique fashion to produce such localized spectra. This work was described in a publication entitled "Local Infrared Microspectroscopy with Sub-wavelength Spatial Resolution with an Atomic Force Microscope Tip Used as a Photo-thermal Sensor" Optics Letters, Vo. 30, No. 18, Sep. 5, 2005. Those skilled in the art will comprehend the details of the technique in the publication but the technique will be described briefly herein for clarity.

Figure 1:
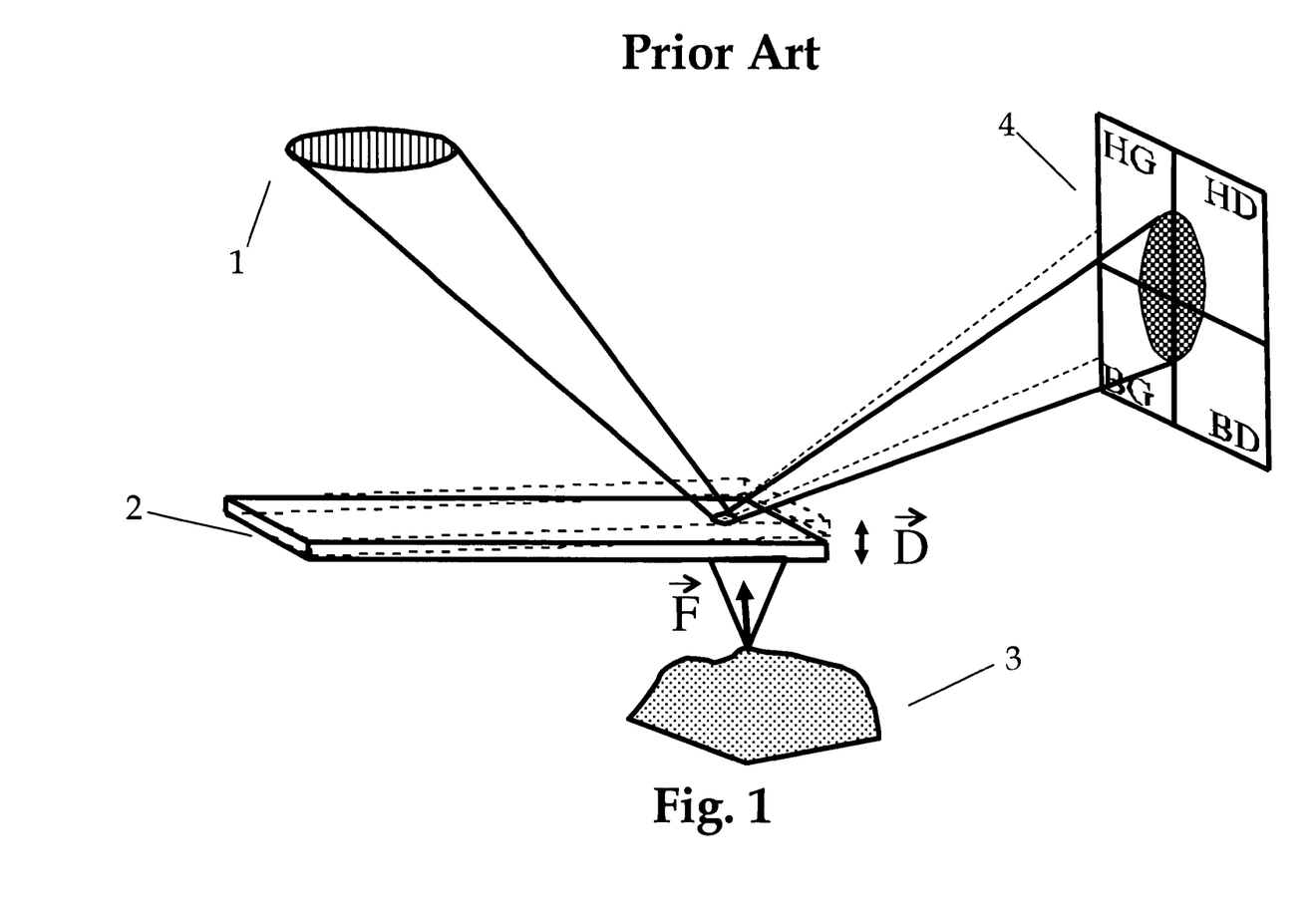
FIG. 1 shows schematically the operation of an AFM.

AFM's are known in the art. The important aspects of an AFM for the current invention are shown in FIG. 1. A light beam 1 is directed at an angle to a cantilever arm 2 which reflects the beam to a photo-detector 4. Typically the photo-detector is a 4-quadrant type, and when the cantilever is placed in the AFM the lever is positioned such that the reflected beam is centered on the photo-detector. The cantilever typically has a probe tip in contact with sample 3. Deflection of the cantilever vertically due to contact with the sample causes the beam spot to move on the detector, generating a difference signal from the detector quadrants. This type of AFM setup is called an optical lever arm, and commercially available AFM's using this technique can measure deflections of the lever on a sub-angstrom scale. There are other options to detect the deflection of the cantilever which can also be used, such as optical interferometry. Other deflection detectors may not generate as much information from the sample as the beam deflection detection. Not shown, but typically present in an AFM, is a scanner to move the sample laterally relative to the tip, and feedback electronics which typically servo the sample or tip up and down in response to height variations of the sample to keep the spot centered on the detector. This vertical servo signal vs lateral position creates a topographical map of the surface which in, commercial AFM's, approaches atomic resolution. A wide variety of variations of the AFM exist with different types of probes and so on for measurements other than topography. For instance, in a co-pending application by some of the inventors of this application, a version of an AFM configured to measure thermal properties of a surface is described.

Figure 2:
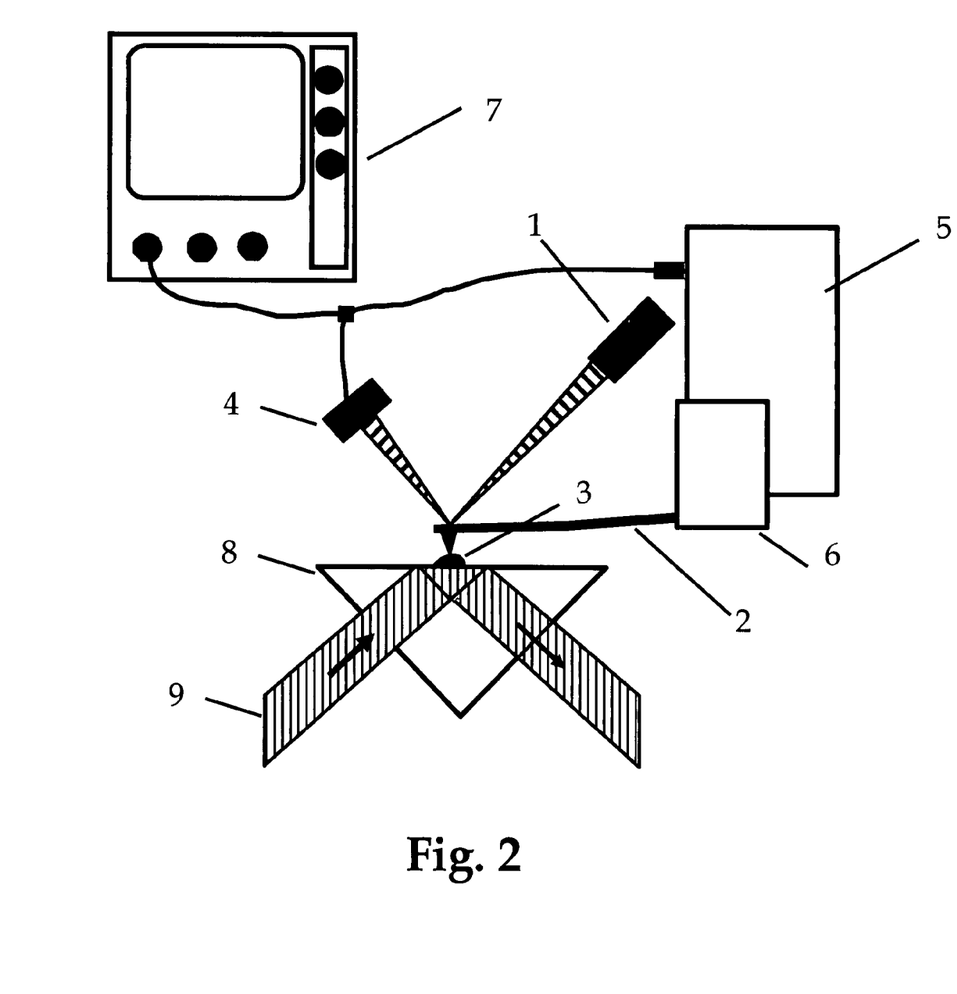
FIG. 2 shows schematically the set-up the laboratory version of the spectroscopy technique.

The AFM set-up used for the published work on IR spectroscopy is shown schematically in FIG. 2. In this set-up, the sample 3 is mounted on a ZnSe prism 8, or prism made from other suitable materials, which does not absorb the radiation of interest. A pulsed IR source 9, in this case a Free Electron Laser beam, is directed into the prism. The prism is made at an angle such that the beam is in Total Internal Reflection in order for the beam to be propagative in the sample and evanescent in the air. Thus only the sample is significantly exposed to the laser radiation, and the AFM probe 2 is minimally exposed to beam 9. The Free Electron Laser (FEL) is an IR source that is both variable in wavelength and has a pulsed output. The probe 2 is placed at a point on the sample by the scanner 6 and is held at an average height by feedback electronics 5. Both the vertical and lateral deflection signal directly from the photo-detector 4, as well as the feedback signal, are monitored at 7.

Figure 3:
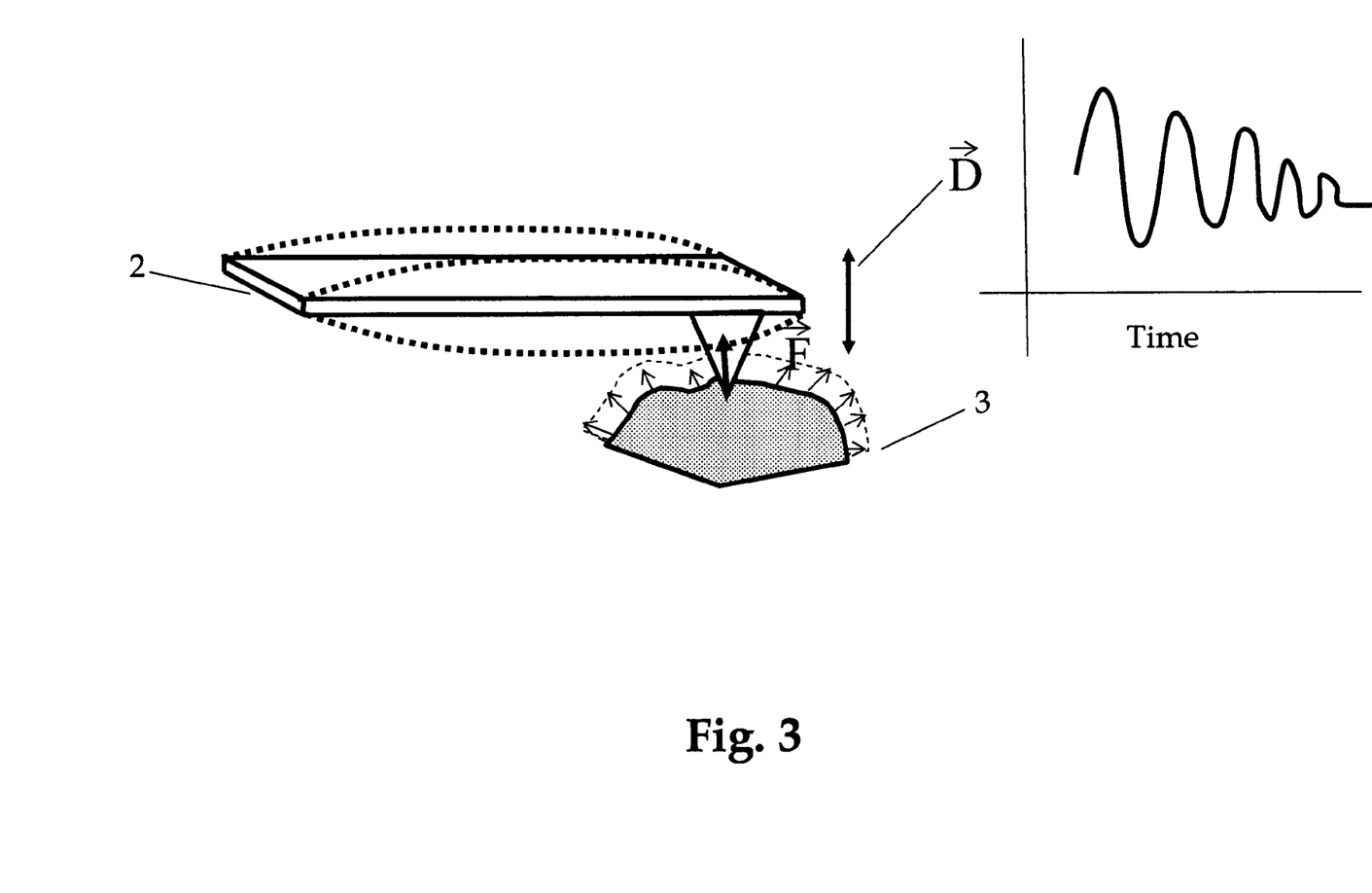
FIG. 3 schematically shows the effect on the cantilever arm when the sample absorbs pulsed IR energy.

Referring to FIG. 3, when the FEL is pulsed, the sample 3 may absorb some of the energy, resulting in a fast thermal expansion of the sample as shown in the Figure. This has the effect of a quick shock to the cantilever arm 2, which if the ability of the cantilever to respond to this shock is slower than the shock will result in exciting a resonant oscillation in the cantilever arm. The resonant oscillation decays as shown in the Figure. Because the FEL energy is ideally contained within the sample, this shock is due primarily to rapid sample expansion as minimal IR energy is absorbed by the cantilever itself. Although the probe is kept in contact with the surface by the feedback electronics, the resonant signal is too fast for the feedback electronics, but can be observed directly from the photodetector. Thus the cantilever rings in the manner shown in FIG. 3 while still in contact with the surface, an effect called "contact resonance". The absolute deflection, amplitude and frequency characteristics of the contact resonance vary with the amount of absorption as well as other properties, such as the local hardness, of the localized area around the probe tip. Also, depending on the direction of the expansion, vertical resonances, lateral resonances or both can be excited. If the tip is to the side of the absorbent material, this will typically cause a stronger lateral response in the cantilever. By repeating the above process at varying wavelengths of the FEL, an absorption spectra on a very localized scale is achieved. By scanning the probe to various points on the sample surface and repeating the spectra measurement, a map of IR spectral surface characteristics can be made. Alternatively, the wavelength of the FEL can be fixed at a wavelength that is characteristic of absorption of one of the components of the sample. The probe can then be scanned across the sample surface and a map of the location of that component can be generated.

Although the set-up as described produced positive results, there is no real possibility of commercializing the set-up as published. For one thing, the requirement to place the sample on a prism to prevent exposing the lever to the IR pulse would limit the possible applications. The actual signals generated can be small thus requiring averaging of the signal and limiting the bandwidth of the technique. More sensitivity would be required to address a wider range of potential samples. Moreover, an FEL is a very expensive and large device and only a few exist in the world. Also, up to this point, the technique is not quantitative in terms of the amount of absorption that occurs in the local area. Determining the absorption from the contact resonance amplitude as well as the measurement of some thermal properties of the sample would improve the ability of the technique to identify materials. Thus a variety of issues must be addressed in order to take the published technique from a laboratory set-up to a commercial analytical instrument. The present invention addresses the commercialization issues.

BRIEF SUMMARY OF THE INVENTION

In one embodiment, the invention is a method of measuring a localized IR spectra of a sample which includes the steps of, illuminating the sample surface with a pulsed variable wavelength IR source, placing an AFM probe at a point on the illuminated surface, collecting lateral and vertical deflection data from the probe due to stimulation of resonant oscillation of the probe in response to a rapid expansion of the surface due to absorption of the illumination in the region of the sample surface under the probe, and measure the amplitude of the deflection signal. This can be done using a simple peak to peak analysis of the data, fitting a sine wave of a specific frequency to the data or by performing a power spectrum of the deflection data of the probe. If performing a power spectrum, typically the data will be integrated over a frequency band of the power spectrum to reduce the data, and, plot the resultant amplitude data vs wavelength to create an IR spectra. Preferably, the spectra may also be taken at a variety of points on the surface by positioning the probe so as to make a spectral map of the surface. Alternatively, the entire deflection data may be taken at one or more points, and then the analysis of the amplitude and frequency characteristics may be selected later, possibly iteratively, to better observe the vertical or lateral deflection data of the cantilever in order to achieve the optimum resolution and discrimination of the spectra or different components of the sample. In some embodiments, a sign is given to the amplitude data indicative of the initial lateral displacement of the probe, which is useful to discriminate between the side of an absorbing material the probe is on. In other embodiments, the deflection data may be collected at one illumination wavelength of interest, rather than taking a spectra, at a variety of points on the sample.

In various embodiments, the invention is a system for measuring a localized IR spectra on a sample surface which includes a pulsed variable wavelength IR source, an AFM, typically consisting of a scanner, provision for mounting of the sample, a cantilever probe with a probe tip, and a cantilever deflection measurement capability. In some of these embodiments, the source is above or below the plane of the sample surface, so all or part of the cantilever probe may be of a material that is transparent to IR radiation so the probe is not affected by absorption itself, but only the sample absorbs energy. Transparent materials include sapphire, silver halides, heavy metal fluoride glasses and chalcogenide glasses. Alternatively, all or part of the cantilever is made to be reflective of IR radiation. Coating all or part of the cantilever with gold is one example of making the probe reflective. Alternatively, the cantilever may be constructed entirely of an IR reflective material.

In certain other embodiments, the system includes a waveguide to direct energy from the source to the surface, thereby avoiding exposing the cantilever to radiation. In some embodiments, the cantilever may be the waveguide.

In other embodiments, the invention is a method of measuring a localized IR spectra of a sample, including placing an AFM probe at a point on the sample surface, illuminating the sample surface with a pulsed variable wavelength IR source, oscillating the probe at a selected frequency in order to collect force distance curves, and identifying how the absorption of radiation influences the shape of a force-distance curve, the way in which the behavior changes as a consequence of the absorption of radiation is called the characteristic behavior.

In various versions, the invention further includes causing the rep rate of the pulsed illumination to be rapid with respect to the imposed oscillation of the probe so that the characteristic behavior is continuously changed. Alternatively, it may be advantageous to cause the rep rate of the pulsed illumination to be slow with respect to the imposed movement of the probe so that the changes in characteristic behavior at the frequency of the pulses can be measured. In another alternative version, it may be beneficial to cause the rep rate of the pulsed illumination and the frequency of the imposed modulation to be set to create periodic interference at the beat frequency, thereby observing the effect on the characteristic force-distance behavior.

In yet another embodiment, the invention is a method of performing the optical absorption type measurements along with quantifying to a reasonable approximation the thermal expansion coefficient or measuring the local thermal diffusivity of a region of the sample. This embodiment would involve combining a temperature controlled probe such as described in co-pending U.S. application Ser. No. 11/405,772, by one of the inventors of this application, incorporated in its entirety by reference. This embodiment further includes placing the thermal probe on a sample, varying the probe's temperature as a pulse or some smooth oscillation, and observing the deflection due to thermal expansion or the temperature due to thermal diffusivity, wherein the data thus acquired can then be used to adjust the relative intensity of the absorption to more accurately reflect the amount of energy absorbed by the sample. Any combination of the absorption and thermal expansion measurements could be made at varying points across the surface to either form complete images or spot checks of either type of data.

BRIEF DESCRIPTION OF THE DRAWINGS

The invention will be better understood by referring to the accompanying Figures.

DETAILED DESCRIPTION OF THE INVENTION

Figure 4:
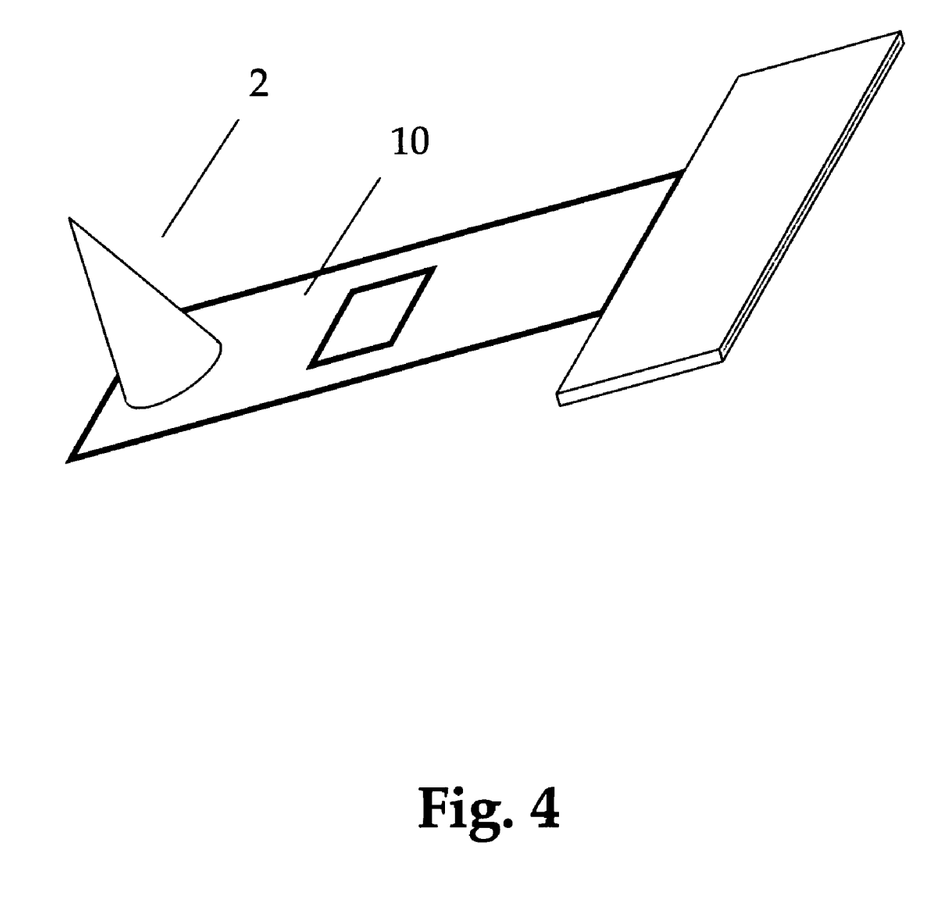
FIG. 4 schematically shows a cantilever which will have a shifted vertical resonance with respect to its lateral resonance.

Referring to FIG. 3, cantilever 2, when shocked by the rapid thermal expansion of the sample rings with both ends basically fixed. This is not the normal deflection mode for an AFM cantilever. Typically an AFM cantilever tip end pivots about the fixed end. Therefore in normal operation the geometry that determines how much signal is generated for a given end deflection is a simple lever arm. For the current case, the deflection is more complex and the design of the cantilever to maximize the signal derived may be different then for a normal AFM cantilever. Moreover, depending on where the probe tip is on the sample, the induced oscillation may have a lateral component leading to a more complex signal. The existence of lateral vibration modes has been shown, and information can be derived from the lateral oscillations as well. The invention includes a cantilever of a specific design so that the contact resonance signal induced by the laser pulse is either amplified at a specific resonance, the various contact resonances are shifted so it is easier to discriminate the vertical versus lateral resonances or both. In the published work, the cantilever used was typically a "V" shaped cantilever in which vertical as well as lateral rapid expansions cause a vertical motion of the laser spot on the photodetector. This can make it difficult to differentiate the two components of the expansion without prior knowledge of the resonant modes of the cantilever. If the probe is on the side of an expanding material due to the IR absorption it will tend to oscillate at a lateral resonance of the cantilever. Differentiating the vertical and lateral components can aid in interpretation of the image as well as localization of the absorbing material which can improve the resolution of the technique. One option to improve the discrimination is to use a "beam" shaped cantilever 2 as shown in FIG. 4, with material removed in the center 10, as opposed to a "V" shaped cantilever. This will have the effect of causing the lateral oscillation of the probe to appear on the lateral deflection signal from the photodetector, separate from the vertical signal and will lower the vertical resonance without having as significant an effect on the lateral resonance in comparison with a solid cantilever.

A major drawback with the laboratory set-up is the need to mount the sample on a prism. This limits the possible applications for a commercial version of the instrument, as it is physically inconvenient to set up such an optical system, and it is not compatible with a range of samples. However, once the Total Internal Reflection set-up is removed, then the issue of the cantilever being exposed to the IR radiation source must be addressed.

Common AFM cantilevers are fabricated using micro-lithography methods out of materials such as silicon and silicon nitride. These materials absorb IR radiation at certain wavelengths. So if such a cantilever is exposed to the laser pulse, the cantilever itself will experience a rapid expansion shock, and it would be difficult or impossible to separate out the data due to the sample from the cantilever itself expanding and the corresponding induced ringing.

Figure 5:
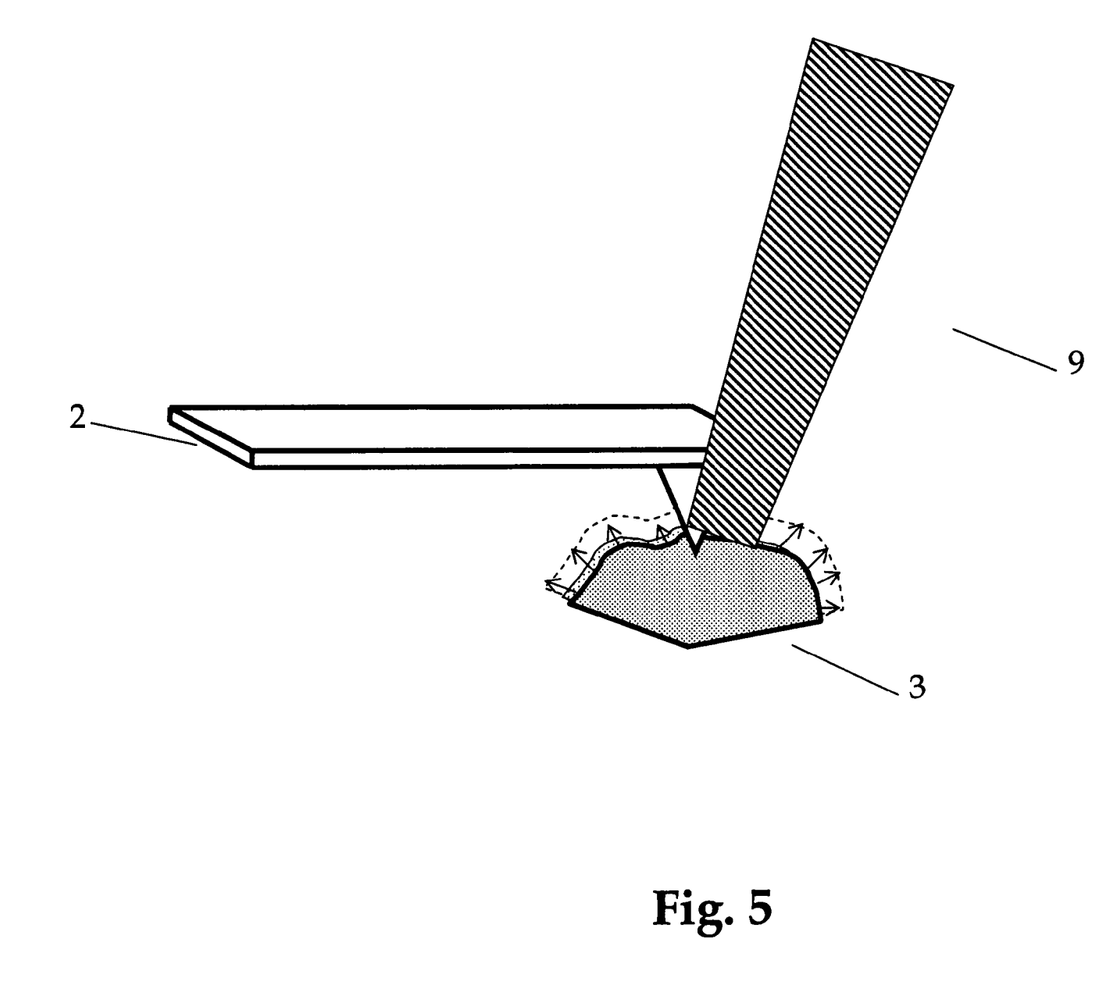
FIG. 5 schematically shows the case where the sample is illuminated from above the plane of the sample.

However, as depicted in FIG. 5 the simplest approach to integrating an IR source with an AFM is to simply mount the source in such a way that the energy 9 comes from above the plane of the sample 2 as shown in FIG. 5. For instance, the source, could be coupled to a relatively simple optical fiber or hollow waveguide that could be easily placed in most AFM's such that the energy came in from an angle and uniformly illuminated the sample. For this case, measures need to be taken to avoid heating up the cantilever along with the sample.

Figure 6:
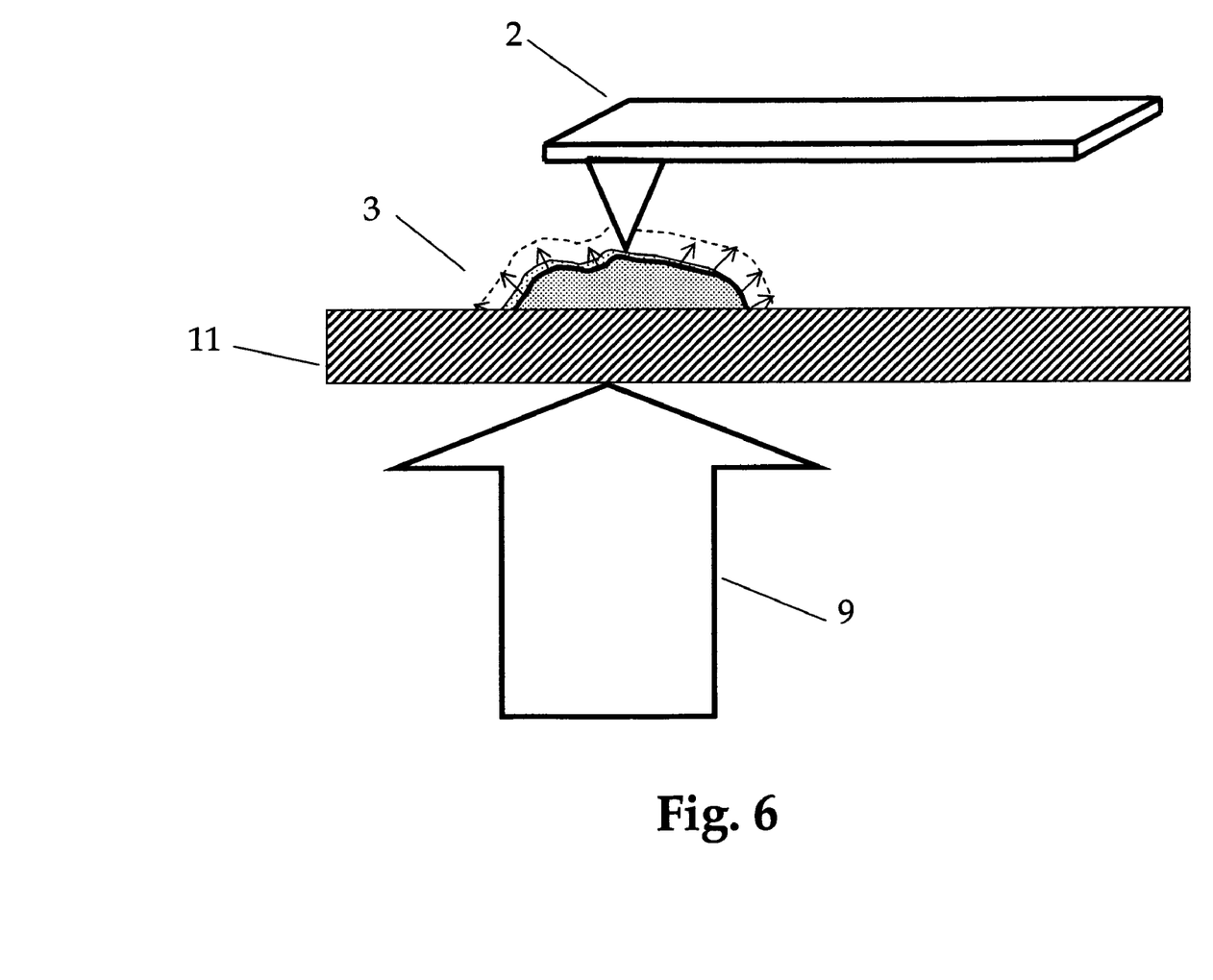
FIG. 6 shows schematically the case where the sample is illuminated from below.

One possible solution is to make the cantilever either all or in part of a material that is suitable from a mechanical standpoint for use as an AFM probe, but is also transparent in the IR. One such material is sapphire which has suitable mechanical properties to be an AFM probe and has been used previously in AFM cantilevers. Unfortunately, sapphire is transparent over a limited range of the mid-IR and so may not be suitable for a number of experiments. Other materials include silver halides, heavy metal fluoride glasses and chalcogenide glasses. These materials do not have the mechanical hardness that sapphire or silicon nitride does, especially the silver halides, so they may have limited lifetime as an AFM probe. Also these materials are not typically used in batch fabrication techniques and so the probes may be more labor intensive to make thus increasing the cost. The chalcogenide glasses do transmit with reasonable losses over the range of interest for this technique and do have reasonable mechanical properties. Also a number of glass, typically silica, probes have been developed for use as AFM probes. While not batch fabricated they do demonstrate the possibility of utilization of these types of probes. As shown in FIG. 6, a transparent cantilever 2 allows for an alternative geometry. If the sample 3 is mounted on an IR transparent substrate 11, such as ZnSe, then the IR illumination 9 may pass through all elements with only absorbent regions of sample 3 actually absorbing any significant amounts of IR energy.

Another potential solution to the geometry of FIG. 5 is to make all or part of the cantilever reflective in the IR, to avoid absorption. The inventors have found that coating the lever with gold can minimize absorption by the cantilever. Typically the coating needs to be thick enough to prevent significant absorption which can cause the end radius of the probe to be large. This may require that the probe be fabricated from the reflective material as opposed to a coating. A number of designs have been developed which incorporate metallic probes on cantilevers including sharpened metallic wires.

Figure 7:
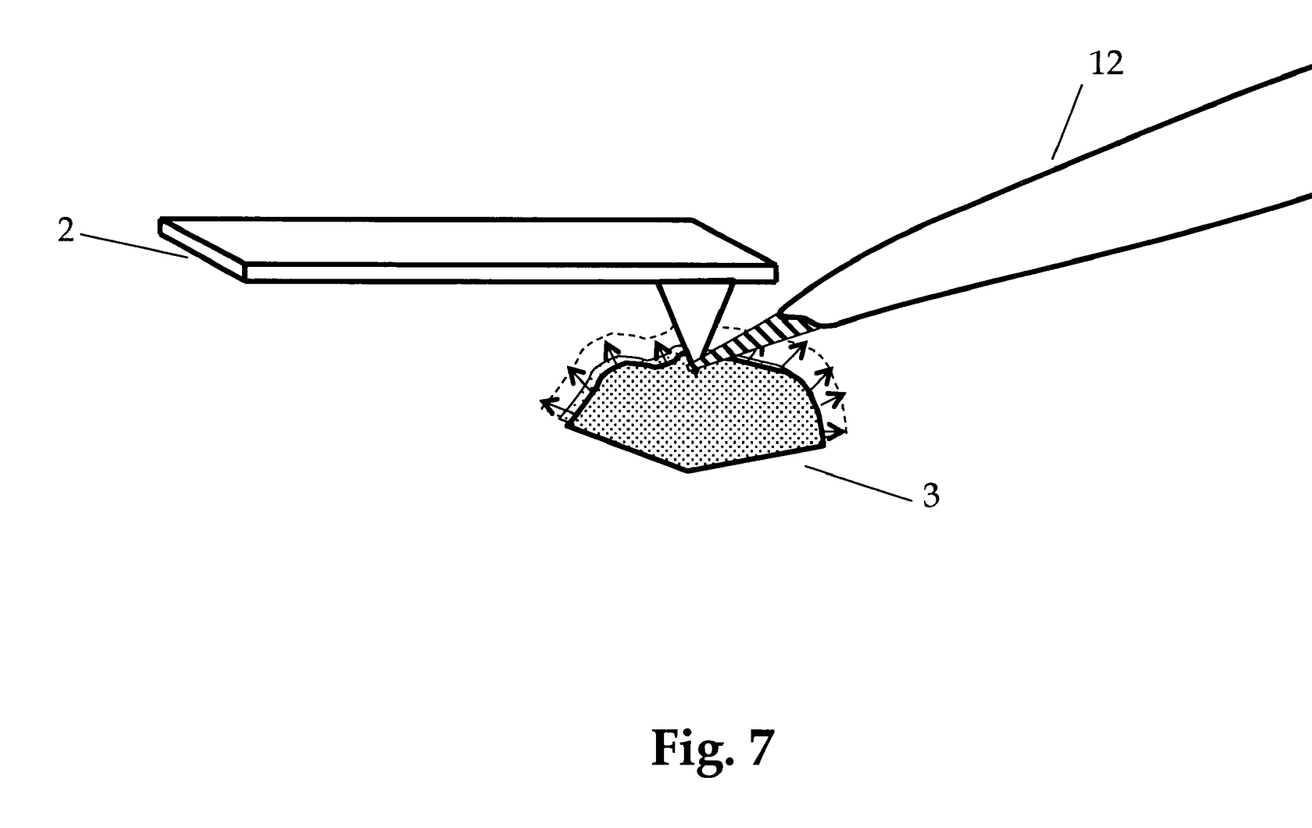
FIG. 7 shows schematically the case where the sample is illuminated through a waveguide.

Another viable, although somewhat more difficult geometry is shown in FIG. 7. In this case, the laser source is coupled to a waveguide 12 that is tapered down to a small diameter and placed right adjacent the probe tip, in such a way that only the sample surface and the end of the probe is illuminated. A pulled end of an optical fiber is an example of a waveguide that could be so mounted. Such an approach has the advantage that a smaller region of the sample is illuminated, thereby reducing mechanical coupling between the expansion in the area of the probe tip and other parts of the sample, possibly resulting in higher effective spatial resolution. It is difficult to prevent all illumination, particularly of the probe tip, using the waveguide technique, so it may be desirable to combine the waveguide with either a transparent or reflective cantilever, or at least part of a cantilever. For instance, a normal material lever arm could be made, but the tip could be a sharp piece of sapphire bonded to the arm. In this case, the tip would be transparent, and the arm would be well away from the waveguide. This form of tip has been developed and is available using a diamond probe that is typically 50-100 um tall and is bonded or welded to the cantilever thus giving ample room for illumination of the sample surface while preventing significant illumination of the cantilever.

The cantilever itself could be a waveguide. Specialty versions of AFM's have been made with a pulled fiber as the probe. Typically these are focused on illumination in the visible range but some groups have demonstrated IR fibers as waveguides for local illumination of the sample with mid IR for an optical based detection technique. Another possibility is a hollow waveguide coated internally with gold such as could be made from a pulled glass pipette.

To be commercially viable, an analytical instrument needs to be robust and reliable. Thus improved data collection processes are needed beyond what is disclosed in the publication. The inventors have found the following preferred data collection process to produce superior results:

illuminating the sample surface with a pulsed variable wavelength IR source,
    placing an AFM probe at a point on the illuminated surface,
    collecting lateral and vertical deflection data from the probe due to stimulation of resonant oscillation of the probe in response to a rapid expansion of the surface due to absorption of the illumination in the region of the sample surface under the probe,
    performing a power spectrum of the oscillation data,
    integrating over a frequency band of the power spectrum, plotting the integrated data vs wavelength to create a spectra.

The Power Spectrum is integrated over a band because the contact resonance frequency will shift as the probe scans along the sample surface due to changes in the contact area between the probe tip and sample and also due to hardness variations in the material that is in contact with the sample. Alternatively, the IR illumination could be fixed in terms of wavelength at a wavelength that is characteristic of one of the components of the sample surface and the probe could be scanned across the sample surface. The method can collect the full deflection signal, the power spectrum of the deflection or just the integrated data. Collecting the full deflection data or power spectrum allows the selection of frequency band to be done after data collection iteratively as the spectra or image is being displayed. Thus the band can be optimized on the vertical or lateral fundamental or higher mode of the cantilever to achieve the optimum resolution and discrimination of the spectra or different components of the sample.

Figure 8:
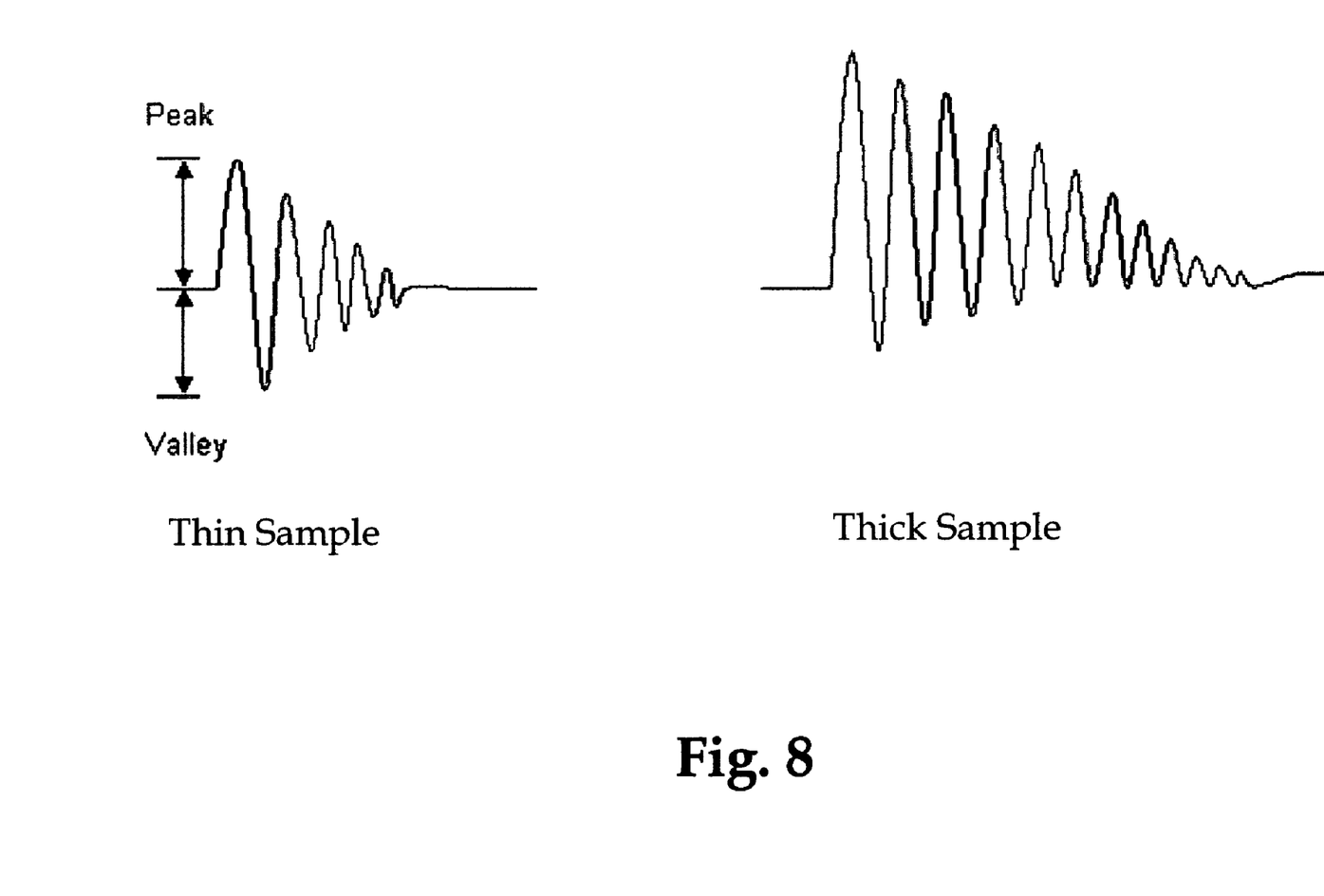
FIG. 8 shows alternative variations on the reaction of the cantilever to the thermal expansion of the sample.

Other analysis techniques besides obtaining a power spectrum of the deflection data may also be of interest. A sine wave could be fit to the deflection data. Another option is to measure the deflection signal before the laser pulse and compare that with the peak amplitude both positive and negative after the pulse as shown in the right side of FIG. 8. This provides a sign for the signal as well as determines if there is any asymmetry to the signal. It has been observed that with increasing sample thickness the induced resonance will be on top of a slower expansion of the sample surface. This will cause the initial expansion upwards to be much larger than the motion down, as shown in the left side of FIG. 8. Thus a peak and valley measurement may also yield thermal expansion data on thicker samples without the need for a heated probe, as described below.

The inventors have also found that more signal can be generated if the pulse frequency of the source is at or near the resonant frequency of the lever, effectively creating a driven oscillator as opposed to a decaying oscillation. The present state of the art however does not provide IR sources with high enough frequency pulse rates to accommodate all cantilevers of interest. In that case, two sources may be used together, offset in phase to generate a higher rep rate.

The IR source used in the laboratory set-up is an FEL. An FEL is one of the only IR sources that can be continuously tuned across wavelength, as is necessary to generate a spectrum. However, other than this attribute an FEL is poor choice in every other way. They are large expensive and complex devices, only existing in a few locations in the world. Therefore they are totally impractical as a source for a commercial version of the technique. Moreover they are limited as to rep rate. Therefore other sources such as an Optical Parametric Oscillator (OPO) or tunable Quantum Cascade laser could be used. OPO's convert monochromatic laser radiation (pump) into a tunable output via a three-wave mixing process with quantum conversion efficiencies that can exceed 50%. The heart of an OPO is a nonlinear-optical crystal. In this crystal, the pump photon decays into two less energetic photons (signal and idler) so that the sum of their energies is equal to that of the pump photon. By careful design of the crystal it is possible to change the wavelength of the IR radiation by moving the crystal and/or controlling its temperature. More than one crystal is typically needed to cover the full mid-IR range.

Turning to other embodiments, the probe could be oscillated at a selected frequency and the way the energy imparted to the sample from absorption on the incident radiation interacts with the motion of the probe can be a sensitive measure of the absorption properties of the sample. For example the force distance curve can be influenced by the energy imparted to the sample, particularly at the moment that probe is being pulled away from the surface as absorbing energy can cause the measured pull-off force to change. Other changes are possible that are more subtle and might require detailed analysis of the force distance curve using standard techniques. These changes in the characteristic behavior (shape) of the force curve due to absorption of the incident radiation are measurable. The pulses of radiation could be very rapid with respect to the imposed oscillation of the probe so that the characteristic behavior is continuously changed, or slow with respect to the imposed movement of the probe so that the changes in the characteristic behavior at the frequency of the pulses can be measured, or the frequency of the imposed modulation and the pulses could be designed to create periodic interference at the beat frequency (heterodyne approach). One way of measuring force distance curves is by pulsed force mode (PFM) AFM. Another is often called force volume imaging.

One option to quantifying the absorption is to use a probe which has a faster response. If the probes response is fast enough, it will follow the rapid thermal expansion of the sample by deflecting as opposed to oscillating. This would allow the characterization of the local expansion which in turn could be used to determine the local temperature rise. Alternatively, the power spectrum could be integrated over a broader range to include the oscillation at all modes of the cantilever, the lateral and vertical signals could be normalized to each other and then the two could be summed. This should give a value equivalent to the initial deflection of the sample due to the IR pulse. It is important when doing this that the laser spot on the photodetector is centered as closely as possible which will optimize the sensitivity and improve the normalization. Thus images could be generated which are either the integrated band of the vertical power spectrum, the integrated band of the lateral spectrum or the normalized sum of the two.

Another option to improve the lateral signal is to use the integrated band of the power spectrum but add a sign to the signal that is dependent on whether the initial change in the deflection of the lateral signal is up or down. If the probe tip is on one side of an expanding material it will initially bend in the opposite direction than if it is on the other side of the material. This will also improve the localization of the material and the interpretation of the image.

Combining optical absorption measurements with thermal expansion measurements, such as described in co-pending application Ser. No. 11/405,772, can assist in analysis of the local absorption properties of the sample. In this case the probe, or possibly a second probe, would be of a thermally controlled type such as described on the co-pending application, and making thermal expansion measurements along with absorption measurements. It is possible that these could be sequential measurements or they could be simultaneous measurements. It has been demonstrated that the resonant signal can be seen in probes that can also measure the local temperature of the sample surface. This has the benefit that the absorption can be measured both by the resonant signal and by the local temperature rise of the sample surface. The combination of these two measurements as well as the possibility to measure the local thermal conductivity and thermal diffusivity of the sample with the thermal probe can improve the quantification of the signal as well as reduce potential artifacts. An example of this is demonstrated by the case where the probe is scanned across the sample surface at a fixed wavelength. The resonant signal could vary in amplitude due to variations in material that absorb the radiation of interest but could also vary due to variations in thermal conductivity in underlying layers causing reduced rapid expansion and therefore reduced resonant signals. Another factor that could cause variation in the absorption signal is the change in Young's modulus over the surface of the sample. The material could have similar chemical characteristics but due to the structure of the material (amorphous or crystalline) would have a different modulus. This will definitely impact the frequency of the induced oscillation in the cantilever and may impact the amplitude. Due to this, it may be beneficial to map the modulus variation across the image and also use this as a correction factor.

We claim:

1. Method of measuring a localized IR spectra of a sample comprising:
    illuminating sample with pulsed variable wavelength IR radiation with an optical parametric oscillator as an IR source;
    placing an AFM probe on the sample;
    collecting deflection data from the probe due to exciting a resonant oscillation of the probe in response to thermal expansion of the sample due to absorption of radiation from the IR source; and,
    repeating the collecting step while varying IR radiation wavelength to create an IR absorption spectrum from the deflection data.

2. Method of claim 1 further comprising scanning the probe to various points on the sample surface and repeating the data collection and spectra creation steps.

3. Method of claim 1 wherein a pulse frequency of the IR source is chosen to be at or near a contact resonant frequency of the AFM probe.

4. Method of claim 1 further comprising the step of measuring a relative thermal expansion coefficient of the region of sample by varying the probe's temperature; and, observing at least one of the deflection due to thermal expansion or the temperature due to thermal diffusivity.

5. System for measuring a localized IR spectrum on a sample surface comprising:
    a pulsed, variable wavelength optical parametric oscillator as an IR source disposed to illuminate the sample; and,
    an AFM, including a scanner, provision for mounting of the sample, a cantilever probe with a probe tip, and a cantilever deflection measurement capability.

6. System according to claim 5 wherein at least a part of the cantilever probe is transparent to IR energy from the IR source.

7. System according to claim 5 wherein at least a part of the cantilever probe is reflective to IR energy from the IR source.

8. System according to claim 5 wherein at least at a part of the cantilever probe is at least one of coated with or constructed of metal.

* * * * *